United States Patent [19]

Edwards et al.

[11] Patent Number: 5,533,531
[45] Date of Patent: Jul. 9, 1996

[54] ELECTRONICALLY ALIGNED MAN-MACHINE INTERFACE

[75] Inventors: Glenn R. Edwards; Stuart J. Rothenberg, both of Palo Alto; Mark L. Oberman, Sunnyvale, all of Calif.

[73] Assignee: Greenleaf Medical Systems, Palo Alto, Calif.

[21] Appl. No.: 294,073

[22] Filed: Aug. 22, 1994

[51] Int. Cl.⁶ .................................................. A61B 5/00
[52] U.S. Cl. .................................................. 128/782
[58] Field of Search ............................. 128/774, 782, 128/779, 781; 73/865.4

[56] References Cited

U.S. PATENT DOCUMENTS

| | | | |
|---|---|---|---|
| 4,414,537 | 11/1983 | Grimes | 340/365 R |
| 4,414,984 | 11/1983 | Zarudiansky | 128/774 |
| 4,444,205 | 4/1984 | Jackson | 128/782 |
| 4,542,291 | 9/1985 | Zimmerman | 250/231 R |
| 4,715,235 | 12/1987 | Fukui et al. | 73/862.68 |
| 4,804,001 | 2/1989 | McLeod | 128/782 |
| 4,972,074 | 11/1990 | Wright | 250/227.11 |
| 4,986,280 | 1/1991 | Marcus et al. | 128/774 |
| 5,047,952 | 9/1991 | Kramer et al. | 364/513.5 |
| 5,086,785 | 2/1992 | Gentile et al. | 128/782 |
| 5,166,462 | 11/1992 | Suzuki et al. | 84/600 |
| 5,184,009 | 2/1993 | Wright et al. | 250/227.11 |
| 5,184,319 | 2/1993 | Kramer | 364/806 |
| 5,228,454 | 7/1993 | Siegler | 128/782 |
| 5,316,017 | 5/1994 | Edwards et al. | 128/782 |
| 5,335,674 | 8/1994 | Siegler | 128/782 |

FOREIGN PATENT DOCUMENTS

| | | |
|---|---|---|
| 115620A | 8/1984 | European Pat. Off. . |
| 60-219501 | 11/1985 | Japan . |
| WO86/01588 | 3/1986 | WIPO . |

*Primary Examiner*—Max Hindenburg
*Attorney, Agent, or Firm*—Kirkpatrick & Lockhart

[57] ABSTRACT

A method of electronically aligning a first sensor having two substantially nonparallel sense axes producing first and second output signals and carried by a garment so as to be positioned proximate to a joint's first axis of movement with a second sensor having two substantially nonparallel sense axes producing third and fourth output signals and carried by the garment so as to be positioned proximate to the joint's second axis of movement, comprises the steps of: reading values for the third and fourth output signals at two points while the joint is moved substantially along only the joint's first axis; electronically combining the third and fourth signals so that the combined output is constant; reading values for the first and second output signals at two points while the joint is being moved substantially along only the joint's second axis; and electronically combining the first and second signals so that the combined output is constant. An apparatus for carrying out the foregoing method is also disclosed.

14 Claims, 12 Drawing Sheets

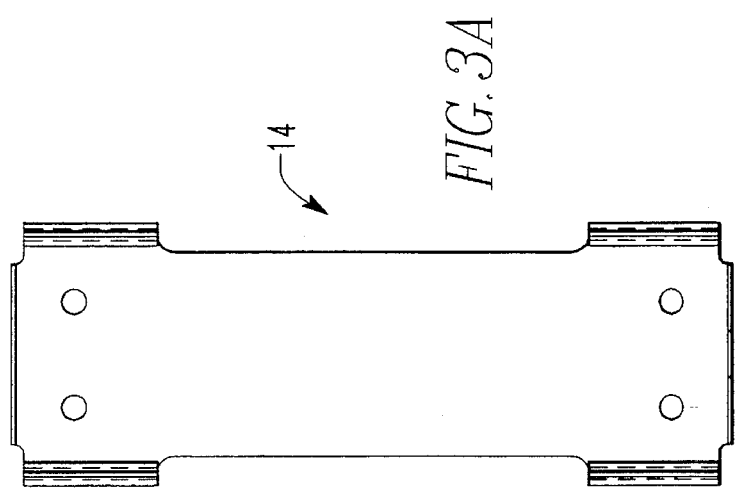
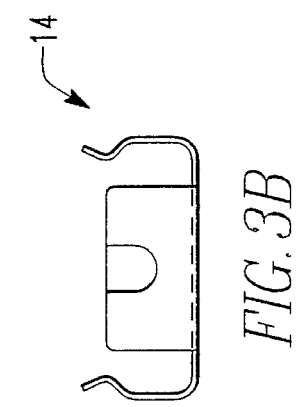

ELECTRONICALLY ALIGNED MAN-MACHINE INTERFACE

BACKGROUND OF THE INVENTION

1. Field of the Invention

The present invention is directed to diagnostic equipment and, more particularly, to diagnostic equipment of the type used to measure range of motion of human joints.

2. Description of the Invention Background

Bio-mechanical research into the intricacies of human body joint movement and the need for a more intuitive approach to man-machine interface requirements are pushing the capabilities of current joint measurement technology. A majority of the human-body joints are multi-axis, rotational hinges. The motion of such multi-axis joints is difficult to accurately track and report. Multi-axis human body joints, such as the wrist, can perform complex movements during the execution of even simple tasks such as tying a knot in a shoestring or turning a door knob. It is critical that the joint measuring apparatus accurately track and report the movements of each axis of the joint. Bio-mechanical research into tendon excursions and repetitive motion injuries depend upon accurate and distinct sensing of each axis.

Alignment of a sensor's axis to a joint's rotation axis is critical to accurately tracking the motion of the joint. What is subtle, and frequently overlooked by technicians in this field, is that the sensor's axis must not only be aligned to the axis that it is sensing, but it also must be aligned with respect to the axis that is not being sensed. That is, a sensor measuring an axis designated as axis 1, must also be aligned to axis 2 in a two axis joint. Alignment of the sensor with respect to axis 2 is required so that movement with respect to axis 2 is not tracked by the sensor. Assuming that the sensor is designed so that it has a well defined sense axis that will not respond to movements orthogonal to that sense axis, off-axis tracking can be eliminated by positioning the sensor responsive to axis 1 orthogonal to axis 2. The sensors described in U.S. Pat. No. 5,316,017 are such sensors.

Physically adjusting the positions of the sensors on, for example, a data glove to eliminate the tracking of off-axis movement is very difficult. Each time a patient dons the data glove, even minute differences in the position of the glove can result in the sensors being positioned in less than the optimal position. The problem is exacerbated further when the same data glove is worn by patients whose body parts may be of different size or disfigured due to accident or illness. A data glove having sensors precisely aligned for one patient, will necessarily require realignment of the sensors for another patient.

Mechanical realignment of the sensors to eliminate tracking of off-axis movement can be tedious, difficult to accomplish and maintain, and, if performed improperly, lead to erroneous results. Accordingly, a method and apparatus for permitting precise alignment of sensors carried by a data glove or other garment so that off-axis movement is not tracked is desirable.

SUMMARY OF THE INVENTION

The present invention is directed to an apparatus for measuring movement in a joint having first and second axes of movement. The apparatus comprises a garment configured to be worn about the joint. A first sensor has two substantially nonparallel sense axes and is carried by the garment so as to be positioned proximate to the joint's first axis of movement. The first sensor produces two output signals. A second sensor has two substantially nonparallel sense axes and is carried by the garment so as to be positioned proximate to the joint's second axis of movement. The second sensor also produces two output signals. Circuitry is provided for combining the two output signals of the first sensor so that the combined output is responsive to substantially only movement occurring along the first axis and for combining the two output signals of the second sensor so that the combined output is responsive to substantially only movement occurring along said the axis.

The present invention is also directed to a method of electronically aligning a first sensor having two substantially nonparallel sense axes and carried by a garment so as to be positioned proximate to a joint's first axis of movement with a second sensor having two substantially nonparallel sense axes and carried by the garment so as to be positioned proximate to the joint's second axis of movement. The first sensor produces first and second output signals. The second sensor produces third and fourth output signals. The method comprises the steps of:

reading values for the third and fourth output signals at two points while the joint is moved substantially along only the joint's first axis;

electronically combining the third and fourth signals so that the combined output is constant;

reading values for the first and second output signals at two points while the joint is being moved substantially along only the joint's second axis; and electronically combining the first and second signals so that the combined output is constant.

By electronically combining the two output signals from each sensor, the sensors can be electronically aligned with the joint's axes without physically having to move the sensors. That represents a substantial advance over the art. With the present invention, a single garment can be used on patients of different size or patients having disfigured joints because the sensors are automatically, electrically aligned to the axes of the joint. Other features of the present invention, such as removable, modular, sensor packs allow a single higher cost sensor pack to be used with a number of lower cost garments sized for different sized patients. Those and other advantages and benefits of the present invention will be apparent from the Description of a Preferred Embodiment hereinbelow.

BRIEF DESCRIPTION OF THE DRAWINGS

For the present invention to be clearly understood and readily practiced, the present invention will be described in conjunction with the following figures wherein:

FIGS. 3A–3C are three views illustrating the proximal saddle attachment;

DESCRIPTION OF A PREFERRED EMBODIMENT

The present invention is directed to man-machine interfaces which can be used to measure the range of motion of joints, particularly joints which have two axes. Although the present invention is described in terms of a data glove used to measure range of motion of the human wrist, the reader will understand that the present invention may be employed in connection with other garments suitable to be worn around other joints so that range of motion data for joints other than the wrist can be gathered.

Figure 1:
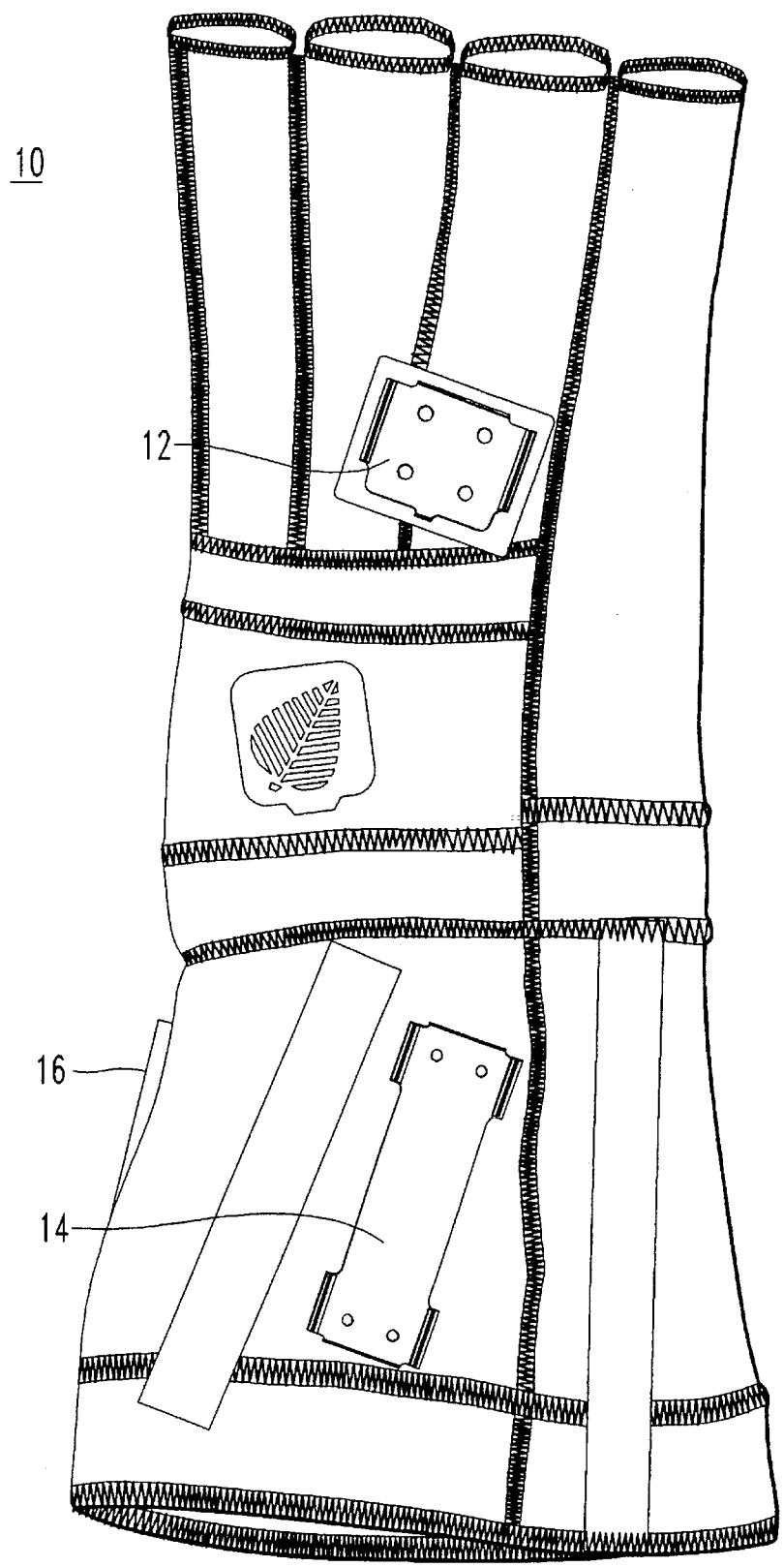
FIG. 1 illustrates a garment referred to as a data glove.

Referring to FIG. 1, a garment 10 is shown which is intended to be worn by the patient. In FIG. 1, the particular garment illustrated is referred to as a data glove although, as mentioned, other types of garments suitable for use with other joints are included within the scope of this invention.

The data glove 10 carries a distal attachment saddle 12. The data glove 10 also carries two proximal attachment saddles 14 and 16 positioned to align with the two primary movement axes of the wrist. In FIG. 1, proximal attachment saddle 16 is only partially visible. However, the construction and operation of saddle 16 is identical to that of saddle 14. All of the attachment saddles 12, 14, and 16 are rigidly attachment to garment 10.

Figure 2A:
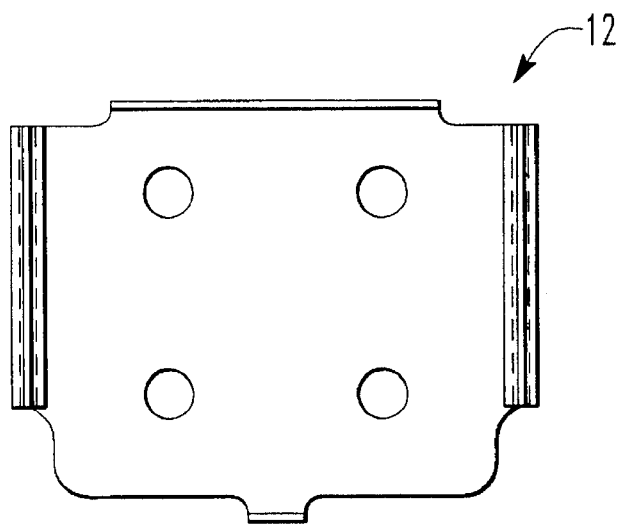
FIGS. 2A–2C are three views illustrating the distal saddle attachment.
Figures 2B, 2C:
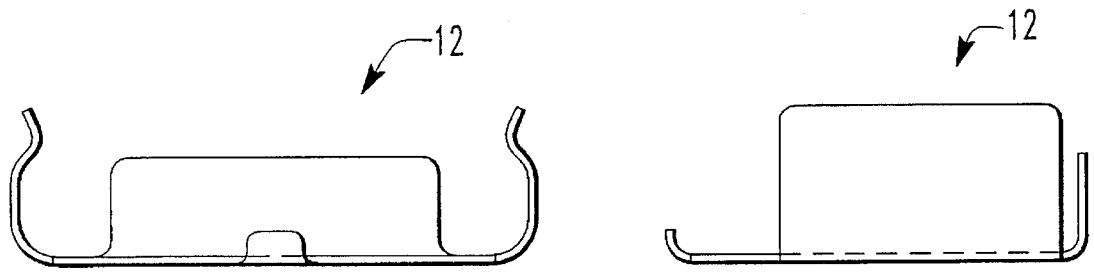

Details of the distal attachment saddle 12 are illustrated in FIGS. 2A through 2C. Details of the proximal attachment saddles 14 and 16 are illustrated in FIGS. 3A through 3C. The particular mechanical configuration of the attachment saddles 12, 14, and 16 is not critical to the present invention provided the functionality, as discussed below, is satisfied.

Figure 4:
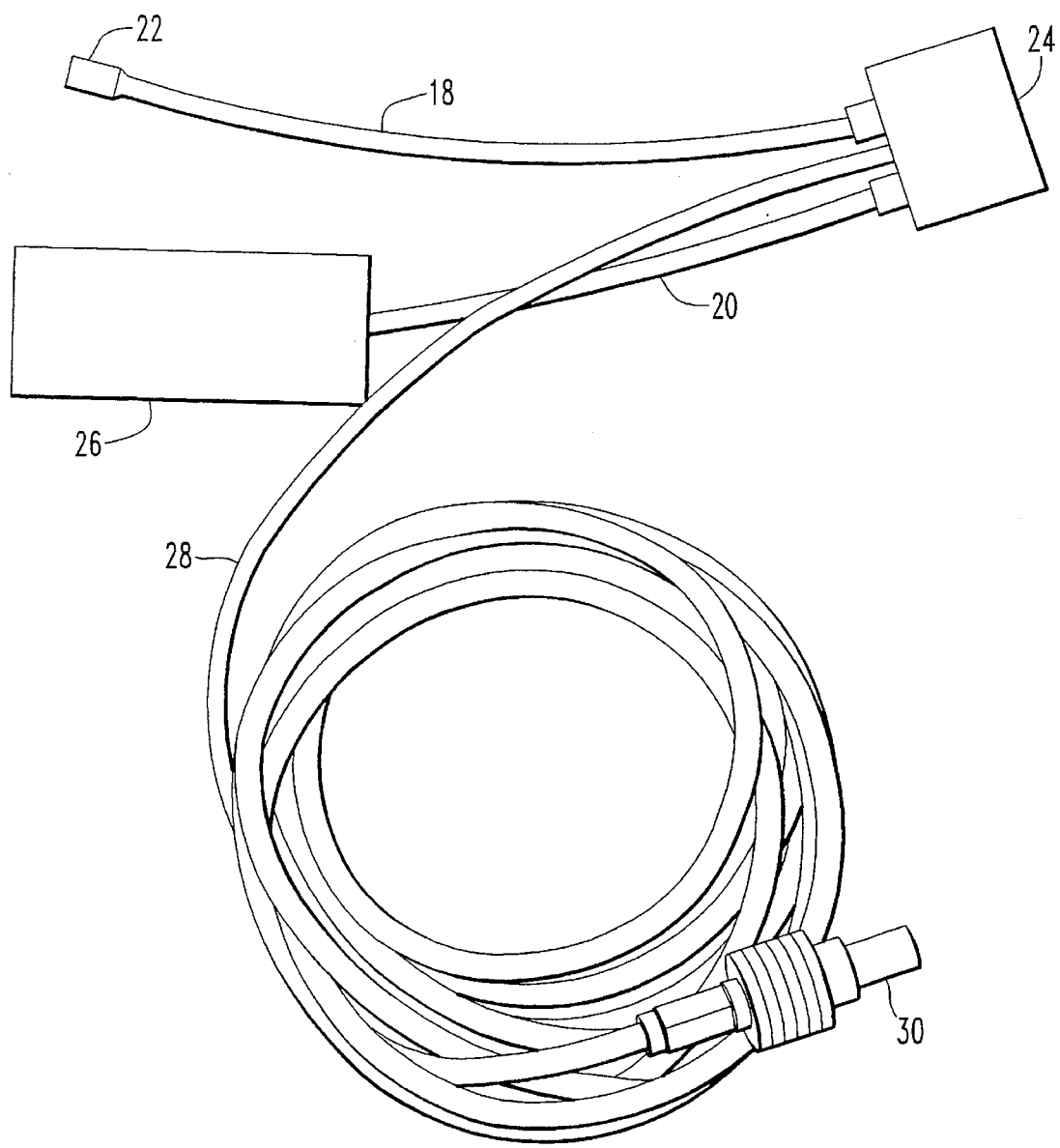
FIG. 4 illustrates a sensor pack comprised of two sensors, one distal end, two proximal slide bearings (only one being shown), a cable, and a cable connector.
Figure 5C:
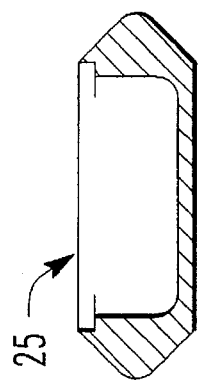
FIGS. 5A–5E are five views illustrating the distal end of the sensor pack.
Figure 5D:
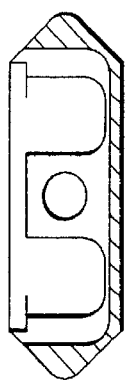
Figure 5E:
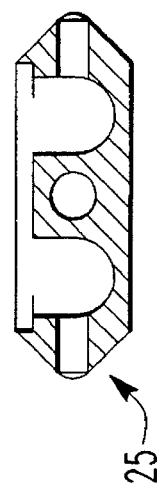
Figure 5A:
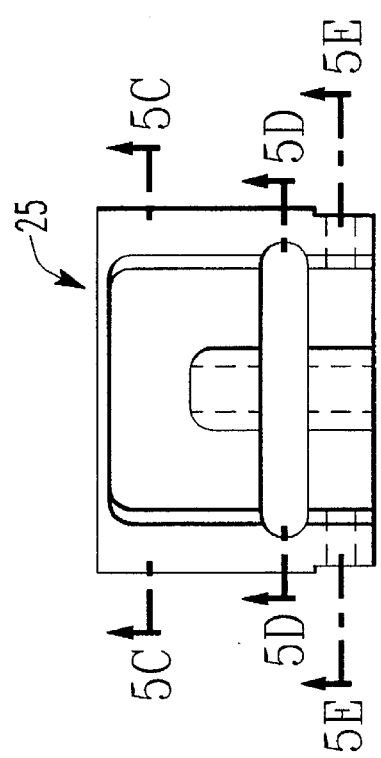
Figure 5B:
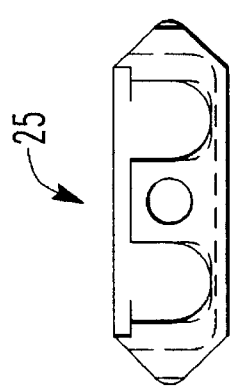

In FIG. 4, a first sensor 18 and second sensor 20 are illustrated. The first sensor 18 has a first end 22 and a second end (not shown) which is housed within the distal end 24 of the sensor pack. The second sensor 20 has a first end (not shown) slidably received within a proximal slide bearing 26 and a second end (not shown) housed within the distal end 24. The reader will understand that the first end 22 of the first sensor 18 is also slidably received by a proximal slide bearing 26, which has been eliminated from FIG. 4 for purposes of illustration.

Figure 6A:
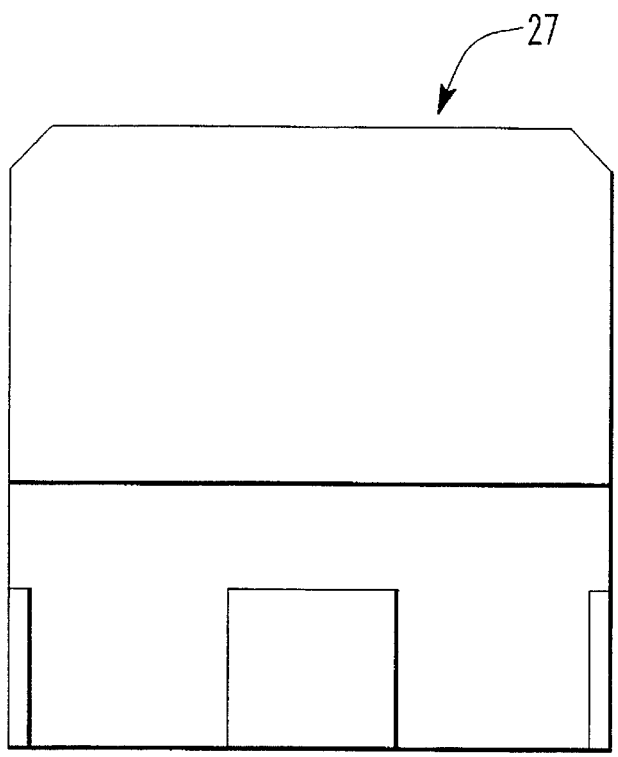
FIGS. 6A–6C are three views illustrating the lid for the distal end of the sensor pack.
Figure 6B:
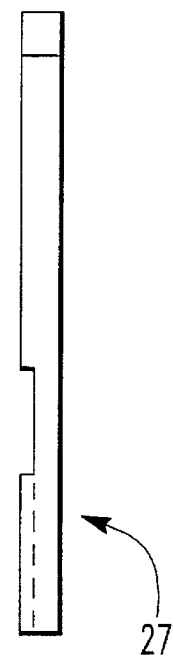
Figure 6C:
Figure 7A:
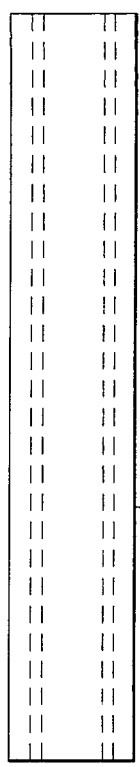
FIGS. 7A and 7B are two views illustrating the proximal slide bearing.
Figure 7B:
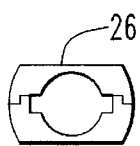

The distal end 24 is comprised of a lower portion 25, the details of which are show in FIGS. 5A through 5E, and a cover 27, the details of which are shown in FIGS. 6A through 6B. The details of the proximal slide bearing 26 are illustrated in FIGS. 7A and 7B. The particular mechanical configuration of the distal end 24 and the slide bearing 26 are not critical to the present invention provided the functionality of each, as discussed below, is satisfied.

The lower portion 25 of the distal end 24 is designed to snap into the distal attachment saddle 12. Because the distal attachment saddle 12 is fixably connected to the garment 10, the distal end 24 is also fixably attached to the garment 10, although it is removable by virtue of the relationship between the distal end 24 and the saddle 12. The first end 22 of the sensor 18 and the first end of the sensor 20 each are each slidably received by a separate proximal slide bearing 26. The proximal slide bearings 26 snap into proximal attachment saddles 14 and 16. In that manner, the proximal slide bearings 26 are fixably attached to the garment while the first ends of sensors 18 and 20 are free to slide within proximal slide bearings 26. Proximal slide bearings 26 are removable from the garment by virtue of the relationship between slide bearings 26 and proximal saddles 14 and 16.

Returning to FIG. 4, also illustrated is a cable 28 and a cable connector 30. Those of ordinary skill in the art will recognize that the cable 28 is suited for delivering power to sensors 18 and 20 and for carrying signals produced by sensors 18 and 20 back to the control electronics.

Figure 8:
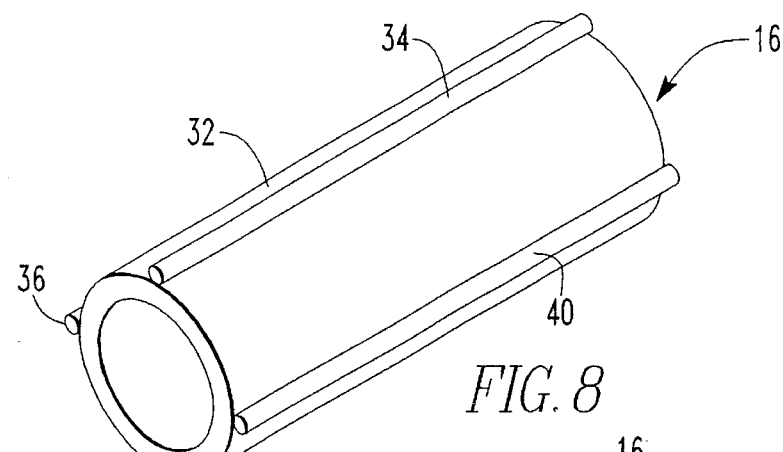
FIGS. 8, 9, and 10 illustrate three different sensor configurations which may be used with the present invention.
Figure 9:
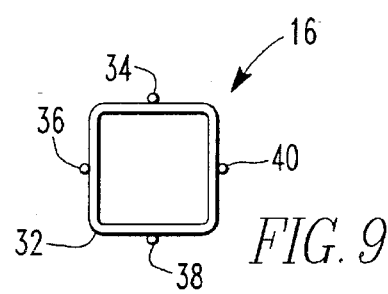
Figure 10:
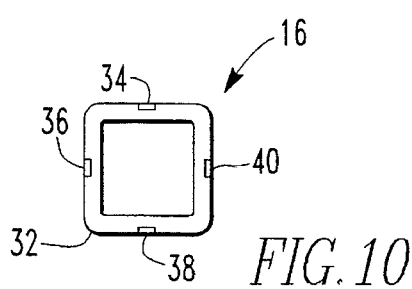

The sensor 18 and 20 of the present invention are each intended to have dual, nonparallel sense axes. Suitable sensor configurations are illustrated in FIGS. 8, 9, and 10. In each of FIGS. 8, 9, and 10, the sensor comprises a sensor beam 32 and four strain gauges 34, 36, 38, and 40. In each case, the strain gauge 34 is electrically connected to the strain gauge 38 to form one sense element while the strain gauge 36 is connected to the strain gauge 40 to form another sense element. Thus, each sensor 18, 20 includes two sense elements. Accordingly, each sensor produces two output signals, $V_{o1}$ and $V_{o2}$.

Figure 11:
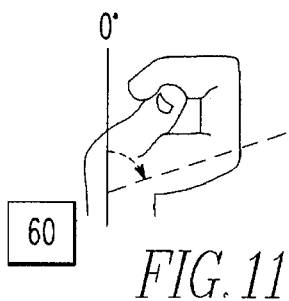
FIGS. 11 and 12 illustrate extension and flexion of the wrist joint, respectively.
Figure 12:
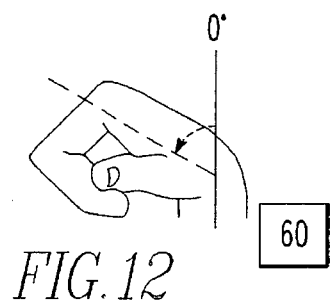
Figure 13:
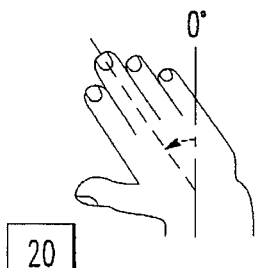
FIGS. 13 and 14 illustrate radial and ulnar deviation of the wrist joint, respectively.
Figure 14:
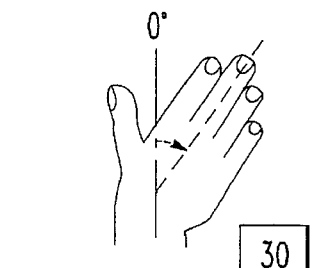

When the components illustrated in FIG. 4 (plus another proximal slide bearing 26 for the first end 22 of the first sensor 18) are connected to the data glove 10, the second sensor 20 will be positioned across the top of the wrist joint while the first sensor 18 will be positioned approximately 90° therefrom, or proximate to the side of the wrist joint. Thus, the second sensor 20 has two sense elements, substantially nonparallel to one another, which are positioned to measure extension and flexion as illustrated in FIGS. 11 and 12, respectively. In a similar fashion, the first sensor 18 has two sense elements, substantially nonparallel to one another, positioned to measure radial deviation and ulnar deviation as illustrated in FIGS. 13 and 14, respectively. The method of the present invention will now be described in conjunction with FIG. 15.

Figure 15:
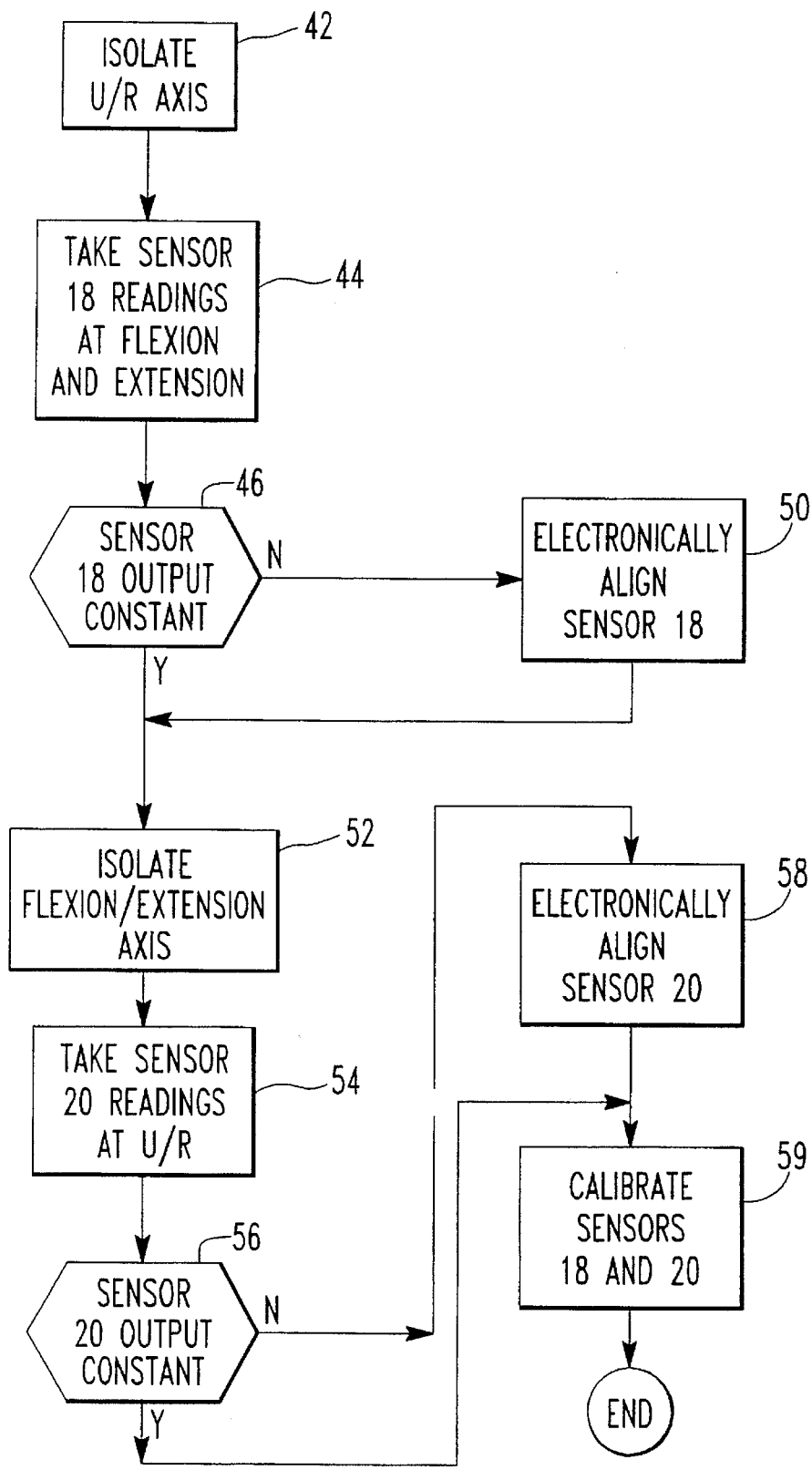
FIG. 15 is a flow chart illustrating the method of the present invention.
Figure 16:
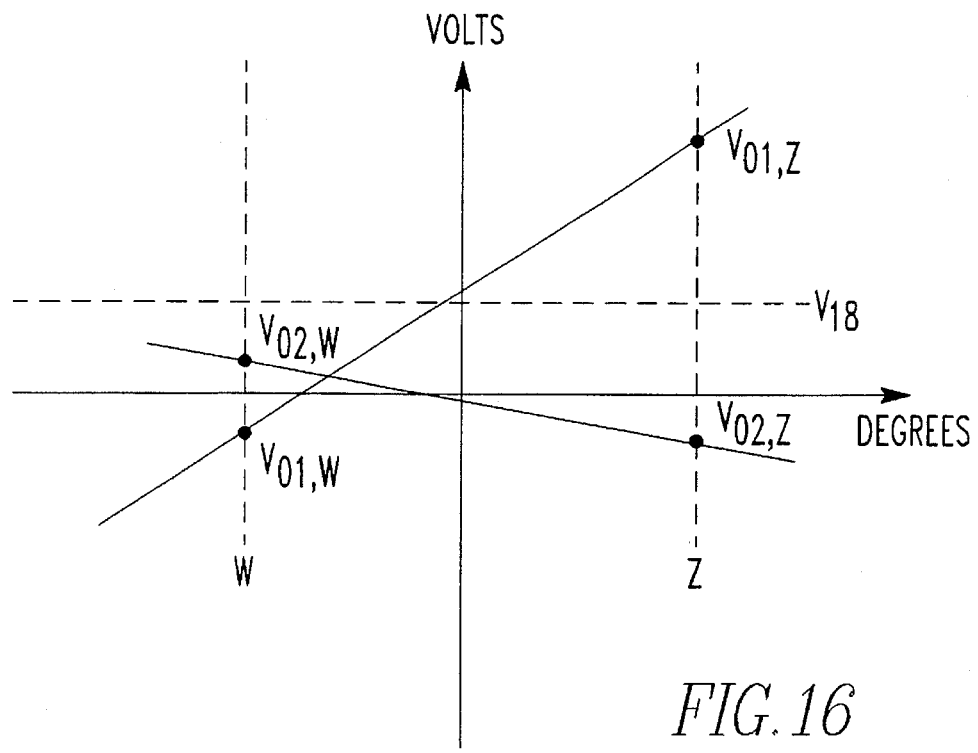
FIG. 16 is a graph of the output signals of a sensor as a function of the degree of bend of the wrist joint.

FIG. 15 is a flowchart illustrating the steps carried out according to the method of the present invention. In step 42, the ulnar/radius joint is isolated by a technician or a specialized fixture so that the wrist may only be moved in an up and down type of motion, i.e., extension-flexion shown in FIGS. 11 and 12. Readings from the two sense elements of sensor 18 are then taken at step 44 for two distinct points, preferably one at a known degree of extension and one at a known degree of flexion, thus generating four readings. The four readings of sensor 18 are analyzed at step 46 to determine if the output of sensor 18 is constant while the wrist is moved in an up and down direction. If the first sensor 18 is properly positioned, and the wrist is properly immobilized so that movement in the radial/ulnar direction is inhibited, then as the wrist is moved in an up and down direction, the output from sensor 18 should not change, i.e. the output should be constant. As a practical matter, the output from the two sense elements of sensor 18 will likely not be constant, and may appear as shown in FIG. 16. In FIG. 16, the output voltage of each active element of sensor 18 is graphed as a function of the degree of bend of the wrist joint.

If the output of sensor 18 is determined to be acceptable at step 46, the process is repeated for the other axis of the wrist beginning at step 52. If the output of sensor 18 is not constant, then the sensor 18 is electronically aligned at step 50 as will be described hereinafter. After electronic alignment at step 50, the method continues with step 52.

Beginning at step 52, the flexion/extension axis is isolated. With the flexion/extension axis isolated, two readings are taken from second sensor 20, preferably at know degrees of radial and ulnar displacement. Because the wrist is immobilized so that it cannot move up and down, the sensor 20 readings should be zero, or a constant. If, at step 56, it is determined that the output of sensor 20 is not a constant, the sensor 20 is electronically aligned at step 58. Thereafter, or if the sensor's 20 output is determined to be constant, the output of sensors 18 and 20 is calibrated at step 59.

Those of ordinary skill in the art will recognize calibration to be a mapping of sensor output voltage to degree of bend. To calibrate sensor output, once the sensors have been properly aligned, measurements are taken on-axis by sensors 18 and 20 at known degrees of bending and the output voltage adjusted to give a desired reading for such known degrees of bending. Thereafter, the process is complete and maybe run again if desired. When the process of the present invention is embodied in software, it is anticipated that the method of FIG. 15 may be carried out iteratively so that alignment and calibration are repeatedly carried out, virtually transparently to the user, so that very high degrees of alignment and calibration can be achieved and maintained.

Figure 17:
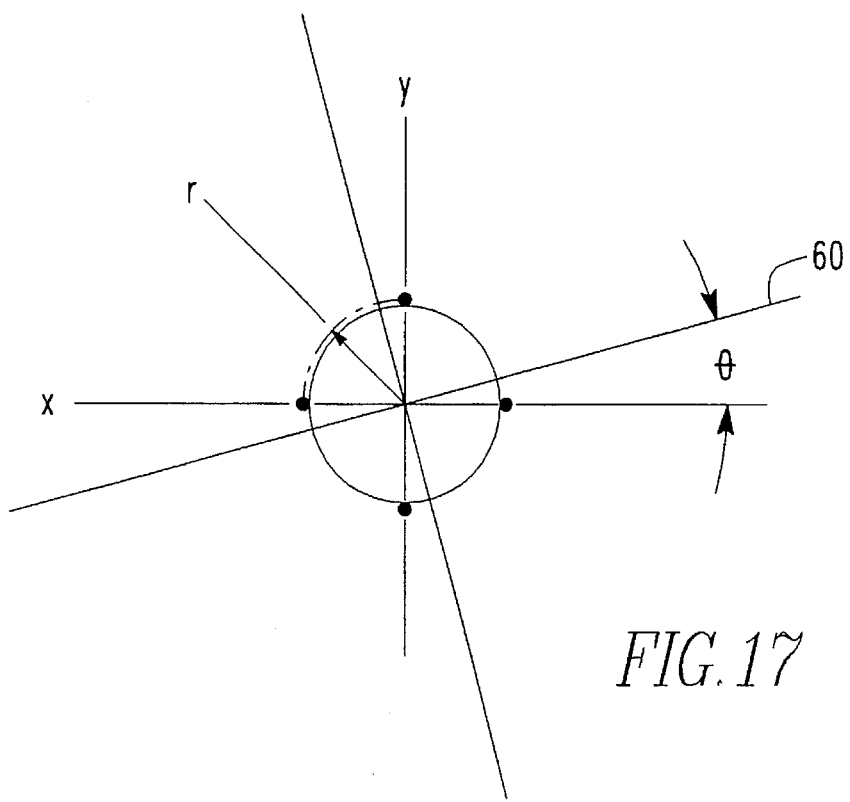
FIG. 17 illustrates the misalignment between a sensor's sense axes and the bend axis of a joint.

An important aspect of the present invention is the electronic alignment which occurs at steps 50 and 58. Turning to FIG. 17, a diagram illustrates the misalignment ($\theta$) between the sense axes (x and y) of the first sensor 18 and the wrist bend axis 60. It is possible to mechanically rotate sensor 18 by $\theta$ to realign sensor 18 such that its sense axes are inline with bend axis 60. However, such mechanical alignment is very tedious, hard to achieve, and hard to maintain. Therefore, the electrical alignment of the present invention represents a substantial advance over the art.

Returning to FIG. 16, assuming a linear output from each of the sense elements, $v_{o1}$ and $v_{o2}$ may be written:

$$v_{o1}=a+bx,$$

and $$v_{o2}=c+dx$$

There are now four unknowns (a, b, c, and d) and four data points, i.e. two measurements taken from sensor 18, and each measurement contains two signals, one from each sense element. The unknowns may be solved as follows:

$$b = \frac{v_{01,z} - v_{01,w}}{z-w}$$

$$d = \frac{v_{02,z} - v_{02,w}}{z-w}$$

$$a = \frac{v_{01,z} + v_{01,w}}{2} - b \cdot ((z+w)/2)$$

$$c = \frac{v_{02,z} + v_{02,w}}{2} - d \cdot ((z+w)/2)$$

Because we are moving the flexion/extension joint, the output of sensor 18 should be constant.

$v_{18}=f$, where f is a constant.
Thus $f=v_{o1}+ev_{o2}$ where e is the rotational constant. The rotational constant e can be determined as follows.

$$e = -\frac{\bar{v}_2 + \frac{\Delta v_2}{\Delta x}(x-\bar{x})}{\bar{v}_1 + \frac{\Delta v_1}{\Delta x}(x-\bar{x})}$$

where
$\bar{v}=\frac{1}{2}(v_{02,z}+V_{02,w})$
$\Delta v_2=(v_{02,z}-V_{02,w})$
$\Delta X=Z-W$
$\bar{x}=(Z+W)/2$
If x=z, then $$e = \frac{-v_{02,z}}{v_{01,z}}$$

If x=w, then $$e = \frac{-v_{02,w}}{v_{01,w}}$$

Once the rotational constant e is determined, the output of the first sensor 18 is electronically aligned, that is, as the wrist joint moves up and down, the output of sensor 18 remains constant as shown by the dotted line in FIG. 16 by virtue of the fact that $v_{18}=v_{o1}+ev_{o2}$.

Figure 18:
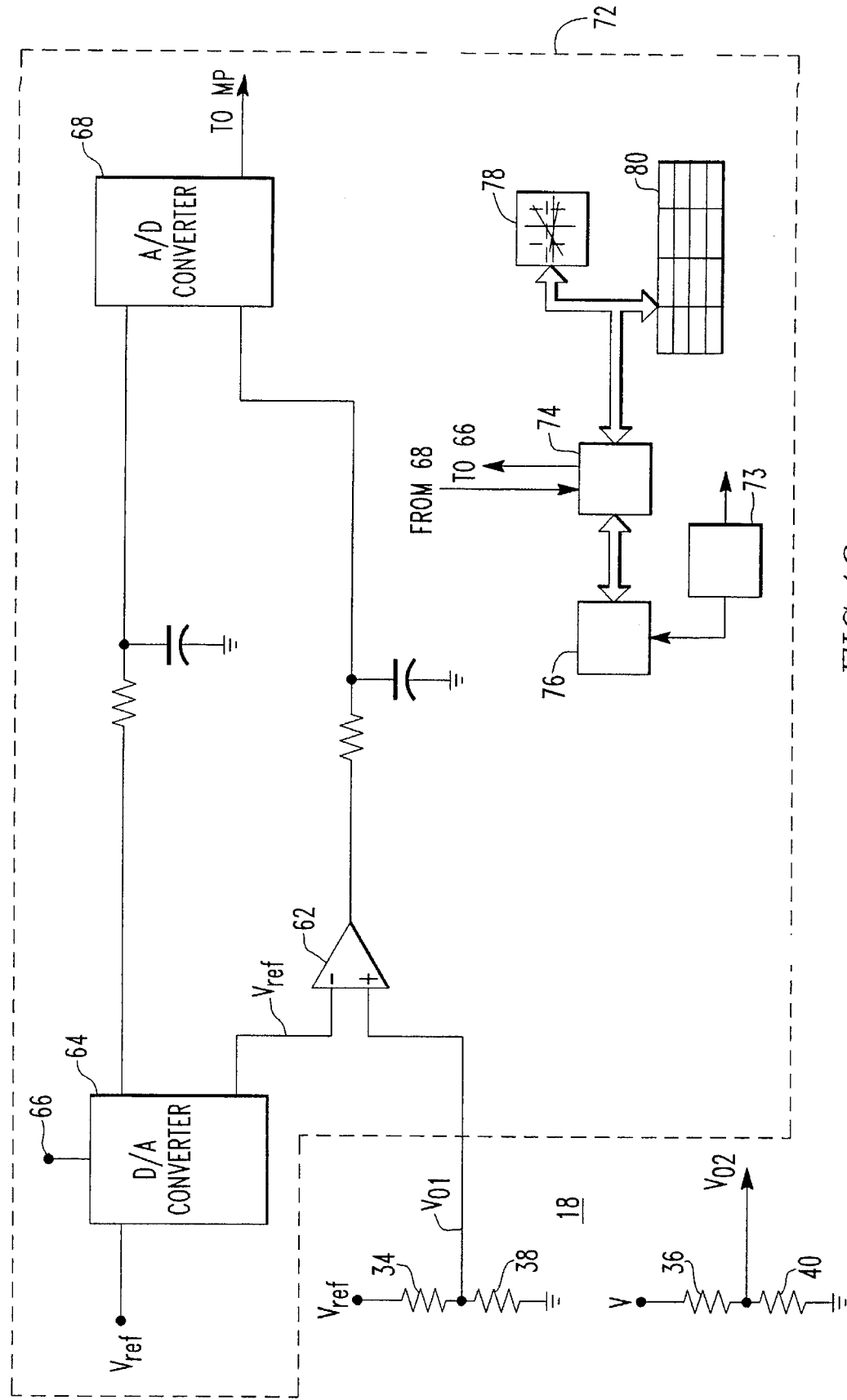
FIG. 18 illustrates an electrical schematic of the present invention.

An electrical schematic of the present invention is illustrated in FIG. 18. In FIG. 18, the strain gauges of sensor 18 are illustrated. The strain gages 34 and 38 combine to form a first sense element while the strain gages 36 and 40 combine to form the second sense element. Circuitry for the sense element formed by strain gages 34 and 38 is illustrated. The reader will understand that similar circuitry is provided for the sense element formed by strain gages 36 and 40 as well as for the second sensor 20.

The output of the first sense element $v_{o1}$ is input to an operational amplifier 62 at its noninverting input terminal. At the inverting input terminal of the operational amplifier 62, a reference voltage produced by a digital to analog (D/A) converter 64 is input. The D/A converter 64 is under the control of either a microprocessor (not shown) or an onboard microprocessor 74 which produces a control signal input at a terminal 66. The control signal input to the terminal 66 is used to control the reference voltage produced by the D/A converter 64 so that the output of operational amplifier 62 is maximized. The output of operational amplifier 62 is then digitized by an A/D converter 68 and the digital information representative of the signal $v_{o1}$ is input to the microprocessor. The microprocessor is programmed to perform the method set forth in FIG. 15 as previously described. The A/D converter 68 and the D/A converter 64 are interconnected as shown in FIG. 18. By virtue of the signal input at input terminal 66, the system is a closed loop system. That is, because the reference voltage input to the operational amplifier 62 is under the control of the microprocessor, the microprocessor has the ability to control the output of the operational amplifier 62 to maintain a high degree of accuracy.

Figure 19:
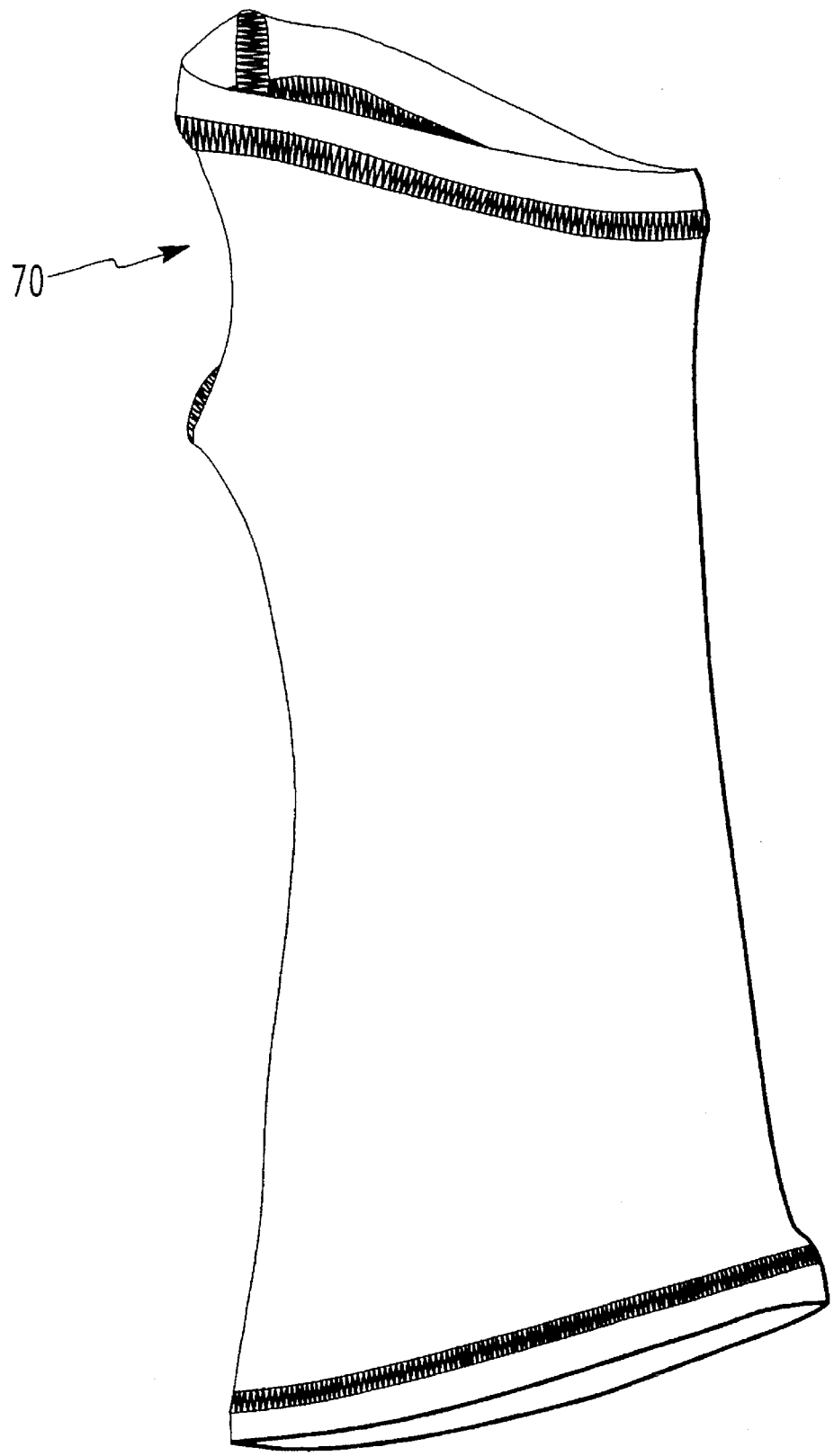
FIG. 19 illustrates an inner liner which may be worn under the garment illustrated in FIG. 1.

To improve performance of the present invention, an inner liner 70, illustrated in FIG. 19, may be used. The inner liner 70 is worn by the patient and is thus interposed between the patient and the garment 10. The incorporation of the inner liner 70 into the design of the present invention accomplishes two goals. First, the inner liner 70 provides a low friction bearing surface between the liner and the main, outer garment 10. That bearing surface allows relative movement between the outer garment 10 and the inner liner 70 which is firmly fixed to the body joint. Allowing relative movement will reduce the amount of cross-talk that is attributable from pronation and supination of the elbow (pronation and supination of the elbow is the rotation of the forearm about the long-axis of the forearm, the primary movement involved in the turning of a door knob). If the inner liner 70 design is not used, pronation and supination will be picked up by any sensor attached to the wrist which will lead to an unwanted signal. The second feature of the inner liner 70 is as a barrier, or contamination control. The inner liner 70 is machine washable, versus hand washable for the outer garment, and is also disposable. The present invention may best be marketed as a reusable device that may be worn by many different persons in the course of its useable life.

Figure 20:
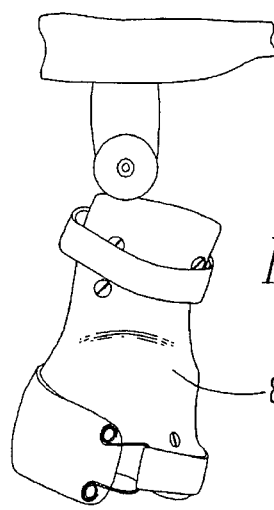
FIGS. 20–22 illustrate a top, bottom, and side view, respectively, of a radial/ulnar fixture which may be used in conjunction with the present invention.
Figure 21:
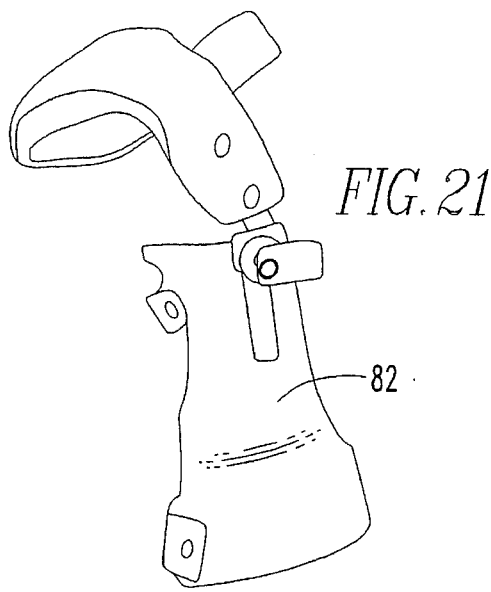
Figure 22:
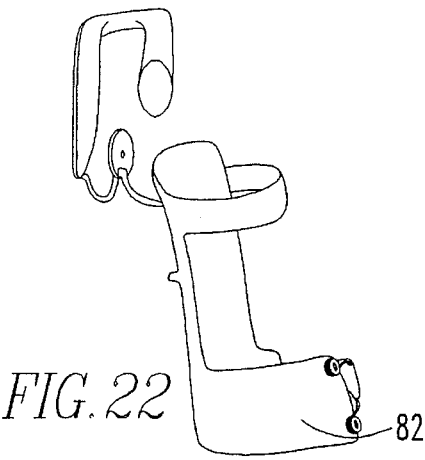

One design of a specialized fixture 82 with which the present invention may be used is illustrated in FIGS. 20 through 22. As seen in the figures, the fixture has only one degree of freedom. When the fixture is attached to a joint, it limits that joint to radial/ulnar movement. In that manner, movement by the joint in the direction of the off-axis is minimized so that accurate electronic alignment and calibration can be achieved.

Figure 23:
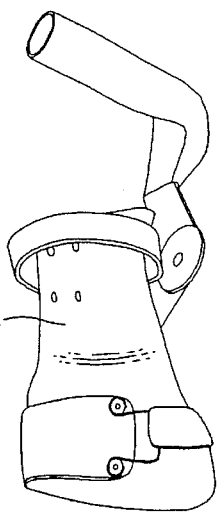
FIGS. 23–25 illustrate a top and two side views, respectively, of a flexion/extension fixture which may be used in conjunction with the present invention.
Figure 24:
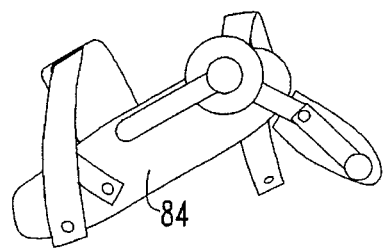
Figure 25:
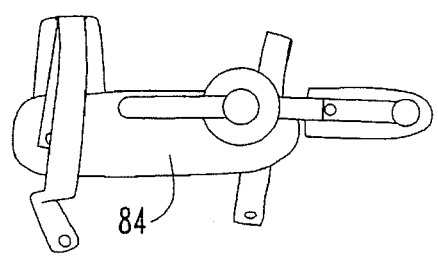

Another design of a specialized fixture 84 with which the present invention may be used is illustrated in FIGS. 23 through 25. As seen in those figures, the fixture has only one degree of freedom-flexion/extension movement. Use of that fixture limits movement in the radial/ulnar direction.

The design of the present invention provides for superior immunity from sensor and wrist axis misalignment, from sensor to sensor misalignment, and from user-induced errors. Through the automatic alignment process, all misalignments are electronically compensated as a result of the performance of the foregoing equations. Further, the user may choose a different set of wrist-rotation axes and perform the exact same alignment procedure but have, as an outcome, the sensors 18 and 20 calibrated to the user-defined wrist axes. That feature is important because medical clinic users of the present invention have a defining set of wrist rotation axes that is different from the bio-mechanical definition of wrist rotation axes, such that the present invention can be manufactured in a single version for use by multiple end users.

By software or firmware span adjustment, a simple user interface and a more accurate sensor calibration results. When a user is performing calibration, he is attempting to provide an accurate mapping of the sensor output, in this case a voltage, to a precise angular rotation input. In essence, associating volts to degrees. That can be a tedious process if the user is required to adjust a trimmer potentiometer to accomplish that task. The present invention's mechanical and electronic design contains no trimmer potentiometer, and achieves span adjustment electronically or through software. The user can concentrate on providing an accurate bend angle input and the electronics and firmware will automatically calculate optimum span adjustment of the sensors according to the fit and function of the individual wearing the garment 10. Firmware span adjustment assures maximum, digital resolution of the sensor output, allows for easy interchangeability of sensors and interface boxes, is superior with respect to compensating for sensor drift, and is superior for adjusting for different sized hands. We accomplish span adjustment during user calibration by incorporating a significantly higher resolution analog to digital converter 68 together with appropriate program code.

Firmware or software offset adjustment allows for a simpler user interface and for a more accurate sensor calibration. The same advantages which are set forth above with respect to span adjustment are also achievable with respect to offset adjustment through the mechanical and electronic design of the present invention.

The present invention is designed with a removable sensor pack as shown in FIG. 4. The sensor pack of FIG. 4 represent a high cost component of the present invention. The sensor packs are designed to fit a variety of garments and garment sizes. Because they are field removable, the customer may purchase the lower cost garment and use the sensor pack of FIG. 4 from another garment therewith. Current state of the art garments have permanently affixed sensors requiring the customer to purchase many garment sizes, each containing the same expensive nonremovable sensors. The modularity of the present invention also allows for easier repair, at a lower cost.

The present invention contemplates the use of an interface box 72 shown by the broken line in FIG. 18. The interface box may contain, in addition to the components already identified in connection with FIG. 18, batteries or other power source 73, a microprocessor 74, a random-access memory 76, a display 78, and a keypad 80 to encourage remote i.e. from the main computer, data collection, data storage, and operator interaction. That is a substantial improvement on existing technology because of the obvious benefits to the customer in terms of portability. Additionally, such a design scheme requires less costly components to be taken into hazardous areas for data collection, areas more likely to be of interest to the medical and ergonomic researcher.

While the present invention has been described in connection with a preferred embodiment thereof, those of ordinary skill in the art will recognize that many modifications and variations are possible. The foregoing description and the following claims are intended to cover all such modifications and variations.

What is claimed is:

1. An apparatus for measuring movement in a human body joint having first and second axes of movement, said apparatus comprising:

garment means configured to be worn about the joint;

first sensor means having two substantially nonparallel sense axes and carried by said garment means so as to be positioned proximate to the joint's first axis of movement, said first sensor producing first and second output signals;

second sensor means having two substantially nonparallel sense axes and carried by said garment means so as to be positioned proximate to the joint's second axis of movement, said second sensor producing third and fourth output signals; and means for electrically combining said first and second output signals so that the combined output of said first sensor means is responsive to substantially only movement occurring along said first axis and for electrically combining said third and fourth output signals so that the combined output of said second sensor means is responsive to substantially only movement occurring along said second axis.

2. The apparatus of claim 1 additionally comprising an inner liner means configured to be worn about the joint and under said garment means.

3. The apparatus of claim 2 wherein said inner liner means and said garment means are constructed of a material which provides a low friction bearing surface therebetween.

4. The apparatus of claim 1 wherein said garment has a plurality of saddles attached thereto, and wherein said first sensor means and said second sensor means each has a distal end and an end opposite to said distal end housed within a separate slide bearing, said distal ends and said slide bearings each being removeably attached to one of said plurality of saddles such that said first sensor is positioned proximate to the joint's first axis of movement and said second sensor is positioned proximate to the joint's second axis of movement.

5. The apparatus of claim 1 wherein said means for electrically combining includes means for determining a first rotational constant such that said first signal plus the result of said first rotational constant times said second signal equals a constant when motion occurs substantially along only said second axis, and means for determining a second rotational constant such that said third signal plus the result of said second rotational constant times said fourth signal equals a constant when motion occurs substantially along only said first axis.

6. The apparatus of claim 1 wherein said first sensor means has two substantially orthogonal sense axes and said second sensor means has two substantially orthogonal sense axes.

7. The apparatus of claim 1 additionally comprising an analog to digital converter means responsive to said output signals, an input device, a microprocessor responsive to said analog to digital converter means and said input device, an output device responsive to said microprocessor, and power supply, means for supplying power to said aforementioned components.

8. The apparatus of claim 8 additionally comprising an interface box for housing said analog to digital converter means, said input device, said microprocessor, said output device, and said power supply means.

9. A method of electronically aligning a first sensor having two substantially nonparallel sense axes and carried by a garment so as to be positioned proximate to a human body's joint's first axis of movement, the first sensor producing a first and a second output signals, and a second sensor having two substantially nonparallel sense axes and carried by the garment so as to be positioned proximate to the joint's second axis of movement, the second sensor producing a third and fourth output signals, said method comprising the steps:

reading values for the third and fourth output signals at two points while the joint is moved substantially along only the joint's first axis;

electronically combining said third and fourth signals so that the combined output is constant;

reading values for the first and second output signals at two points while the joint is being moved substantially along only the joint's second axis; and electronically combining said first and second signals so that the combined output is constant.

10. The method of claim 9 additionally comprising the step of prohibiting movement along the joint's second axis while reading the values for the third and fourth signals and prohibiting movement along the joint's first axis while reading the values for the first and second signals.

11. The method of claim 9 wherein the step of prohibiting movement includes the steps of placing the joint in a fixture having only one degree of freedom along the axis of interest.

12. The method of claim 2 wherein the step of electronically combining said first and second signals includes the step of determining a first rotational constant such that said first signal plus the result of said first rotational constant times said second signal equals a constant when motion occurs substantially along only said second axis.

13. The method of claim 12 wherein the step of electronically combining said third and fourth signals includes the step of determining a second rotational constant such that said third signal plus the result of said second rotational constant times said fourth signal equals a constant when motion occurs substantially along only said first axis.

14. The method of claim 13 additionally comprising the step of electronically mapping the combined output of said first sensor so as to establish a relationship between output voltage and degree of bend of the first axis of the joint and comprising the step of electronically mapping the combined output of said second sensor so as to establish a relationship between output voltage and degree of bend of the second axis of the joint.

* * * * *